United States Patent
Christensen et al.

(10) Patent No.: US 8,066,669 B2
(45) Date of Patent: *Nov. 29, 2011

(54) VASCULAR ACCESS DEVICE HOUSING VENTING

(75) Inventors: Kelly D. Christensen, Centerville, UT (US); Paul R. Johnson, Kaysville, UT (US); Weston F. Harding, Lehi, UT (US); Troy A. Ekberg, Sandy, UT (US); Greg L. Brimhall, West Jordan, UT (US); Tom M. Miner, Alpine, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 130 days.

This patent is subject to a terminal disclaimer.

(21) Appl. No.: 11/935,064

(22) Filed: Nov. 5, 2007

(65) Prior Publication Data

US 2008/0200903 A1    Aug. 21, 2008

Related U.S. Application Data

(60) Provisional application No. 60/864,509, filed on Nov. 6, 2006.

(51) Int. Cl.
*A61M 1/00*    (2006.01)
(52) U.S. Cl. .......................... 604/126; 604/122
(58) Field of Classification Search .................. 604/122, 604/126, 246, 124, 125, 167.01–167.06, 604/168.01, 236–238, 247, 533, 537–539, 604/256
See application file for complete search history.

(56) References Cited

U.S. PATENT DOCUMENTS

| | | | |
|---|---|---|---|
| 4,003,403 A | 1/1977 | Nehring | |
| 4,193,399 A | 3/1980 | Robinson | |
| 4,269,186 A | 5/1981 | Loveless et al. | |
| 4,682,980 A | 7/1987 | Suzuki | |
| 4,765,588 A | 8/1988 | Atkinson | |
| 4,894,052 A | 1/1990 | Crawford | |
| 4,917,671 A | 4/1990 | Chang | |
| 4,935,010 A * | 6/1990 | Cox et al. ....................... | 604/122 |
| 5,032,116 A | 7/1991 | Peterson et al. | |
| 5,226,883 A | 7/1993 | Katsaros et al. | |
| 5,242,411 A * | 9/1993 | Yamamoto et al. ...... | 604/167.04 |
| 5,251,873 A | 10/1993 | Atkinson et al. | |
| 5,295,657 A | 3/1994 | Atkinson | |
| 5,295,658 A | 3/1994 | Atkinson et al. | |
| 5,295,970 A | 3/1994 | Clinton et al. | |
| 5,338,313 A | 8/1994 | Mollenauer et al. | |
| 5,342,316 A | 8/1994 | Wallace | |
| 5,417,664 A | 5/1995 | Felix et al. | |

(Continued)

FOREIGN PATENT DOCUMENTS

EP    0268480    5/1988

(Continued)

*Primary Examiner* — Kevin C Sirmons
*Assistant Examiner* — Laura Schell
(74) *Attorney, Agent, or Firm* — Mony R. Ghose; Kirton & McConkie

(57) ABSTRACT

A Luer access device may include a housing, a septum, and a gas permeable vent in communication with at least a portion of the housing for venting gas from an extravascular system. A method of venting a medical device may include providing a gas permeable vent within a Luer access device as part of an extravascular system and venting gas from the extravascular system through the gas permeable vent of the Luer access device.

8 Claims, 10 Drawing Sheets

U.S. PATENT DOCUMENTS

| | | |
|---|---|---|
| 5,441,487 A | 8/1995 | Vedder |
| 5,474,544 A | 12/1995 | Lynn |
| 5,501,426 A | 3/1996 | Atkinson et al. |
| 5,501,671 A | 3/1996 | Rosen et al. |
| 5,533,708 A | 7/1996 | Atkinson et al. |
| 5,542,932 A | 8/1996 | Daugherty |
| 5,549,651 A | 8/1996 | Lynn |
| 5,919,160 A | 7/1999 | Sanfilippo, II |
| 5,954,657 A | 9/1999 | Rados |
| 5,957,898 A | 9/1999 | Jepson et al. |
| 6,139,534 A | 10/2000 | Niedospial, Jr. et al. |
| 6,171,287 B1 | 1/2001 | Lynn et al. |
| 6,261,282 B1 | 7/2001 | Jepson et al. |
| 6,344,033 B1 | 2/2002 | Jepson et al. |
| 6,503,225 B1 | 1/2003 | Kirsch et al. |
| 6,595,964 B2 | 7/2003 | Finley et al. |
| 6,651,956 B2 | 11/2003 | Miller |
| 6,669,681 B2 | 12/2003 | Jepson et al. |
| 6,866,656 B2 | 3/2005 | Tingey et al. |
| 6,908,459 B2 | 6/2005 | Harding et al. |
| 2002/0193752 A1 | 12/2002 | Lynn |
| 2005/0077225 A1 | 4/2005 | Usher et al. |
| 2005/0256457 A1 | 11/2005 | Rome |
| 2005/0256500 A1 | 11/2005 | Fujii |
| 2008/0097407 A1* | 4/2008 | Plishka .................. 604/533 |
| 2008/0103487 A1* | 5/2008 | Miyasaka ................ 604/537 |

FOREIGN PATENT DOCUMENTS

WO  WO2006037638  4/2006

* cited by examiner

VASCULAR ACCESS DEVICE HOUSING VENTING

RELATED APPLICATIONS

This application claims the benefit of U.S. Provisional Application No. 60/864,509, filed Nov. 6, 2006, entitled VASCULAR ACCESS DEVICE HOUSING VENTING, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously. A group of vascular access and other devices used to access the vasculature of a patient may be collectively referred to as an extravascular system.

One example of an extravascular system including a catheter is the BD NEXIVA™ Closed IV (intravenous) Catheter System, by Becton, Dickinson and Company. This system includes an over-the-needle, peripheral intravascular catheter made from polyurethane, another catheter used as an integrated extension tubing with a Y adapter and slide clamp, a vent plug, a Luer access device or port, and a passive needle-shielding mechanism.

The design of the BD NEXIVA™ IV catheter can be described as a closed system since it protects clinicians or operators from blood exposure during the catheter insertion procedure. Since the needle is withdrawn through a septum that seals, after the needle has been removed and both ports of the Y adapter are closed, blood is contained within the NEXIVA™ device during catheter insertion. The pressure exerted on the needle as it passes through the septum wipes blood from the needle, further reducing potential blood exposure. The clamp on the integrated extension tubing is provided to eliminate blood exposure when the vent plug is replaced with another vascular access device such as an infusion set connection or a Luer access device or port.

A current procedure of initiating the use of an extravascular system such as the BD NEXIVA™ Closed IV Catheter System is as follows. A device operator will insert the needle into the vasculature of a patient and wait for flashback of blood to travel into the device to confirm that the needle is properly located within the vasculature of the patient. The blood travels into and along the catheter of the device because a vent plug permits air to escape the device as blood enters the device. After an operator confirms proper placement, the operator clamps the catheter to halt the progression of blood through the catheter, removes the vent plug, replaces the vent plug with another vascular access device such as an infusion set connection or a Luer access port, unclamps the catheter, flushes the blood from the catheter back into the vasculature of the patient, and re-clamps the catheter.

Many current procedures like the procedure described above present challenges that need to be overcome. For example, the procedure may include an unnecessary number of steps and amount of time to simply insert and prepare an extravascular system for use within the vasculature of a patient. Further, by removing the vent plug, the fluid path of the system is temporarily exposed to potential contamination from the external environment of the extravascular system.

Rather than using a vent plug, some operators attempt to solve the problem above by simply loosening a Luer access device and permitting air to escape from the system during flashback and then tightening the Luer access device to stop blood from advancing along the catheter. Unfortunately, this procedure is also prone to user error, a lack of consistent and accurate control of blood flow through the system potentially leading to blood exposure and loss of body fluids, and unnecessary risk of contamination.

Thus, what are needed are improvements to many of the systems and methods described above. Such systems and methods can be improved by providing more efficient vascular access device housing venting systems and methods.

BRIEF SUMMARY OF THE INVENTION

The present invention has been developed in response to problems and needs in the art that have not yet been fully resolved by currently available vascular access systems, devices, and methods. Thus, these systems, devices, and methods are developed to provide more efficient vascular access venting systems and methods.

A medical device may include a Luer access device having a housing and a septum, and a gas permeable vent in communication with at least a portion of the housing. The gas permeable vent is capable of venting a gas from an extravascular system. The vent may include a porous membrane attached to a vent plug, a porous annular ring integrated into the housing, an annular ring fit within a space of the housing, an annular vent material exposed to the inner surface of the Luer access device, a vent plug and a vent hole, and/or an annular venting membrane secured at least in part by the septum.

The vent may communicate with a vascular access device secured to the Luer access device. The Luer access device may also include a tip, and the vent may be located within the housing of the tip. The Luer access device may include a tip, the vent may be located at least in part within the housing of the tip, and the tip may mate with a female connector of another vascular access device. The vent may be located at least in part within the female connector of the other vascular access device in addition to the housing of the tip of the Luer access device. The Luer access device may also include a tip having a lumen, and the vent may reside within the lumen.

A method of venting a medical device may include providing a Luer access device including a housing and a septum, the Luer access device forming part of an extravascular system, providing a gas permeable vent in communication with at least a portion of the housing, and venting gas from the extravascular system through the gas permeable vent of the Luer access device. The method may also include plugging the vent with a plug. The vent may include a porous annular ring integrated into the housing, an annular ring fit within a space of the housing, an annular vent material exposed to the inner surface of the Luer access device, a vent plug and a vent hole, and/or an annular venting membrane secured at least in part by the septum.

Venting may include placing the vent in communication with a vascular access device secured to the Luer access device. The Luer access device may also include a tip and the vent may be located within the housing of the tip. The method may also include employing a Luer access device that includes a tip with a vent located at least in part within the housing of a tip, and mating the tip with a female connector of a vascular access device, where the vent is located at least in part within the female connector of the vascular access device. The Luer access device may also include a tip having a lumen and the vent may reside within the lumen.

A medical device may include a means for providing Luer access to the vascular system of a patient and a means for venting an extravascular system. The means for providing Luer access to the vascular system of a patient may include a housing and may form part of an extravascular system. The means for venting the extravascular system communicates with the housing of the means for providing Luer access to the vascular system of a patient.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
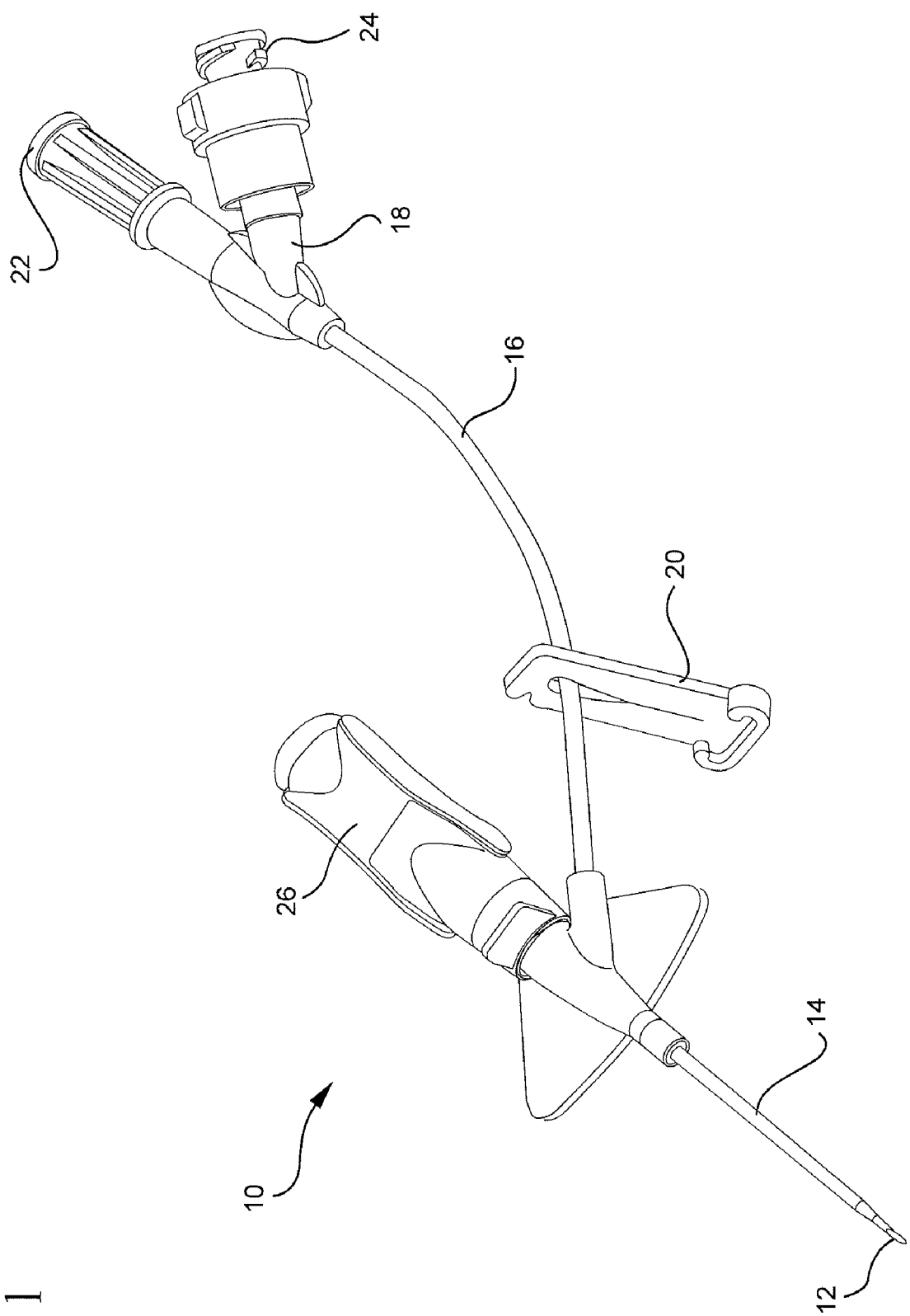
FIG. 1 is a perspective view of an extravascular system of vascular access devices.

Referring now to FIG. 1, an extravascular system 10, such as the BD NEXIVA™ Closed IV (intravenous) Catheter System, by Becton, Dickinson and Company, is used to communicate fluid with the vascular system of a patient. An example of the system 10, as shown in FIG. 1, includes an intravascular needle 12; an over-the-needle, peripheral intravascular catheter 14 made from polyurethane; an integrated extension tubing 16 with a Y adapter 18 and clamp 20; a vent plug 22; a Luer access device or port 24; and a passive needle-shielding mechanism 26. Any adapter used to connect two or more vascular access devices may be used in place of the Y adapter 18.

The system 10 is a closed system since it protects clinicians or operators from blood exposure during the catheter 14 insertion procedure. Since the needle 12 is withdrawn through a septum that seals after the needle 12 has been removed and both ports of the Y adapter 18 are closed, blood is contained within the system 10 during catheter 14 insertion. The pressure exerted on the needle 12 as it passes through the septum wipes blood from the needle 12, further reducing potential blood exposure. The slide clamp 20 on the integrated extension tubing 16 is provided to eliminate blood exposure when the vent plug 22 is replaced with another vascular access device such as an infusion set connection or another Luer access device or port 24.

As mentioned above, a current procedure of initiating the use of the extravascular system 10 is as follows. A device operator will insert the needle 12 into the vasculature of a patient and wait for flashback of blood to travel into the system 10 to confirm that the needle 12 is properly located within the vasculature of the patient. The blood travels into and along the catheter 14 between the wall of the catheter 14 and the needle 12. This occurs because a vent plug 22 permits air to escape the system 10 as blood enters the system 10. After an operator confirms proper placement, and after adequate venting of the system 10 has occurred, the operator clamps the extension tubing 16 to halt the progression of blood through the catheter 14, removes the vent plug 22, replaces the vent plug 22 with another vascular access device such as an infusion set connection or a Luer access device similar or identical to Luer access device or port 24, unclamps the extension tubing 16, flushes the blood back into the vasculature of the patient, and re-clamps the extension tubing 16. Alternate vents and venting procedures are desired and will be discussed with reference to the figures following FIG. 1.

Figure 2:
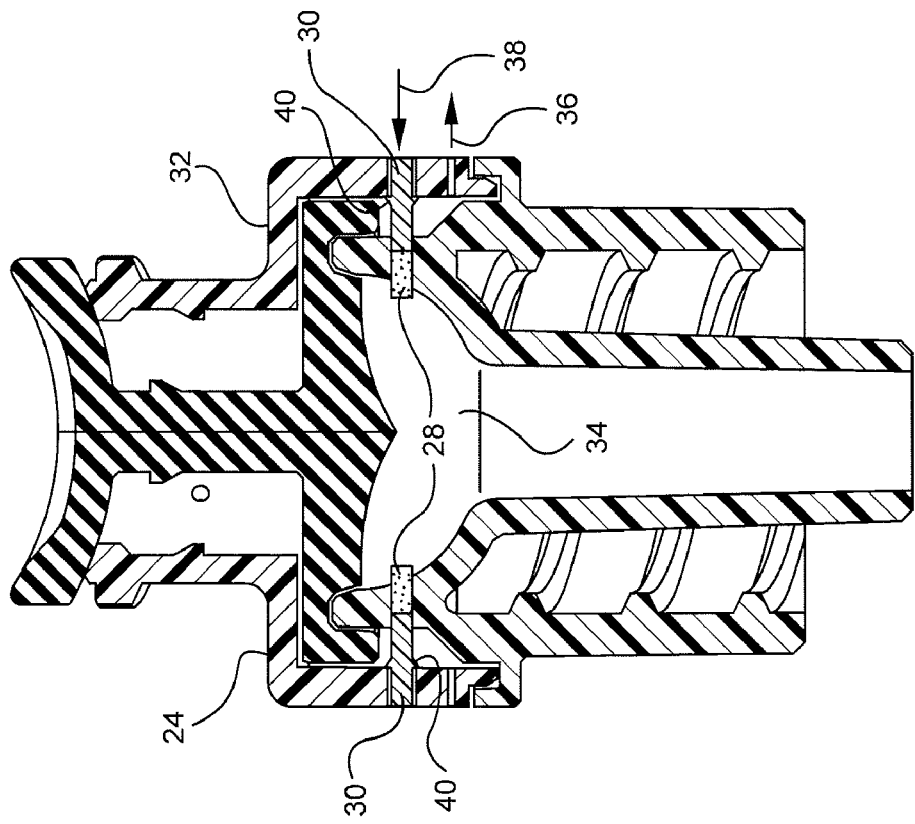
FIG. 2 is a cross section view of a Luer access device having a membrane and a vent plug.

Referring now to FIG. 2, a Luer access device 24 includes a vent with a porous membrane 28 attached to a vent plug 30. The porous membrane 28 is a self-sealing porous membrane located within the housing 32 of the Luer access device 24. The location of the membrane 28 within the housing 32 is such that the membrane 28 is exposed to an internal cavity 34 of the device 24. Since both gas and liquid travels through an extravascular system 10 to which the Luer access device 24 may be attached, the porous membrane 28 may be used to vent gas from the internal cavity 34 through an airflow channel 36 to the external atmosphere in which the device 24 is placed.

The elastomeric plug 30 serves to operate as a potential barrier to the continued flow of air or other gas through the membrane 28 to the external atmosphere. In use, an operator may exert force in a direction 38 against the plug 30, forcing the plug 30 to enter deeper into the housing 32 of the device 24. As the plug 30 travels deeper into the housing 32, the elastomeric properties of the plug 30 cause the plug 30 to compress and force the membrane 28 towards the interior of the device 24, cutting off the air flow channel 36.

Figure 3:
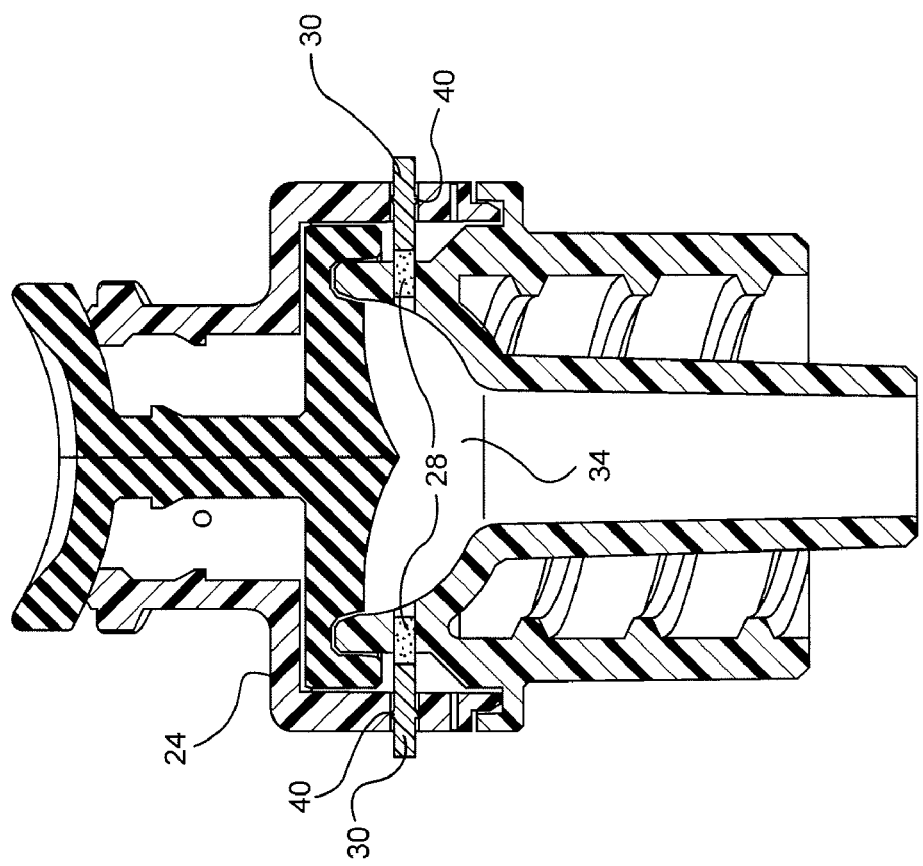
FIG. 3 is a partial cross section view of the membrane and plug of FIG. 2.

Referring now to FIG. 3, a partial cross section view of the membrane 28 and elastomeric plug 30 of the Luer access device 24 of FIG. 2 is shown. The elastomeric plug 30 is shown fully inserted into the housing 32 of the device 24, causing the membrane 28 to have been advanced towards the interior of the device 24 and the air flow channel 36 of FIG. 2 to be cut off. The elastomeric plug 30 includes elastomer barbs or notches 40 on the side surface of the plug 30. The notches 40 communicate with an interior edge of the housing 32, preventing the plug 30 from retracting out of the housing 32 towards the external atmosphere of the device 24. In this manner, the elastomeric plug 30 can seal the membrane 28 permanently after actuation by an operator. Thus, the embodiment described with reference to FIGS. 2 and 3 provide a gas permeable vent in communication with at least a portion of the housing 32 in order to provide a Luer access device 24 that vents a gas from an extravascular system 10.

Figure 4:
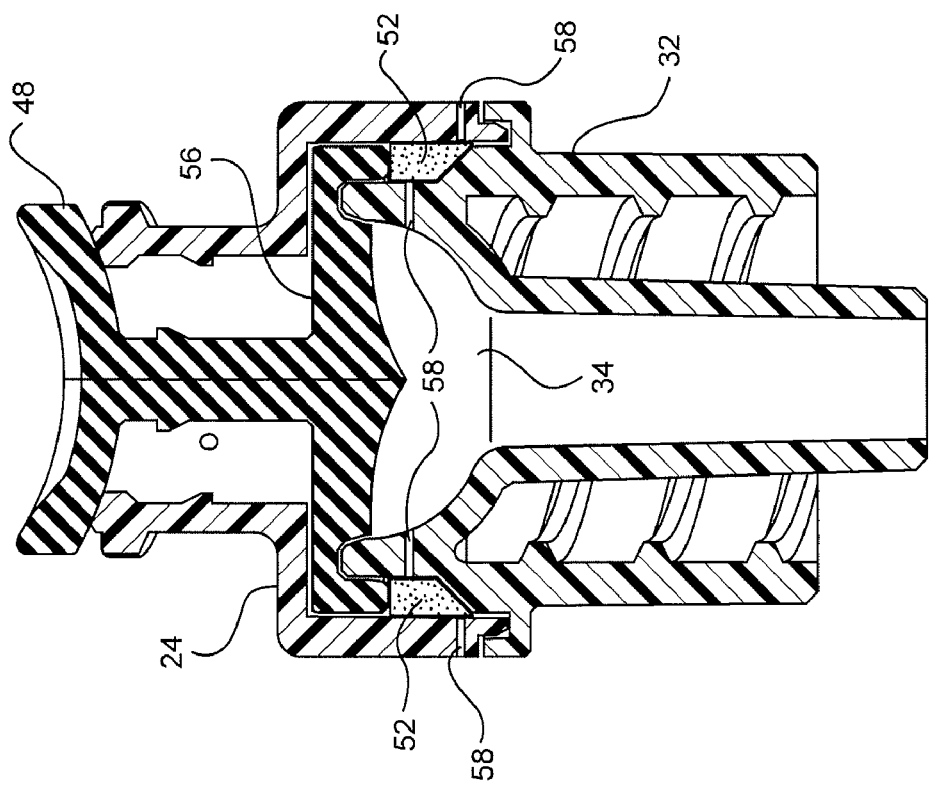
FIG. 4 is a cross section view of a Luer access device including a porous annular ring.

Referring now to FIG. 4, a Luer access device 24 includes a vent with a porous annular ring 42 integrated into the housing 32 of the device 24. The porous annular ring 42 forms a lower notch 44 which communicates with an upper notch 46 of a portion of the housing 32 that is on the interior of the device 24. The porous annular ring 42 may also communicate with a septum 48 located within the Luer access device 24. The porous annular ring 42 provides a vent that is permeable to gas through which gas may escape the device 24 from an internal cavity 34 along an air flow path 50 to the external atmosphere in which the device 24 is located. The porous annular ring 42 is a porous self-sealing ring that is attached mechanically or otherwise bonded to the housing 32 and/or septum 48 of the device 24. The annular ring 42 provides a vent to air flow, but not liquid flow. Thus the annular ring 42 is capable of venting an extravascular system 10 to which the device 24 is attached without permitting any fluid such as blood to escape the closed extravascular system 10.

Figure 5:
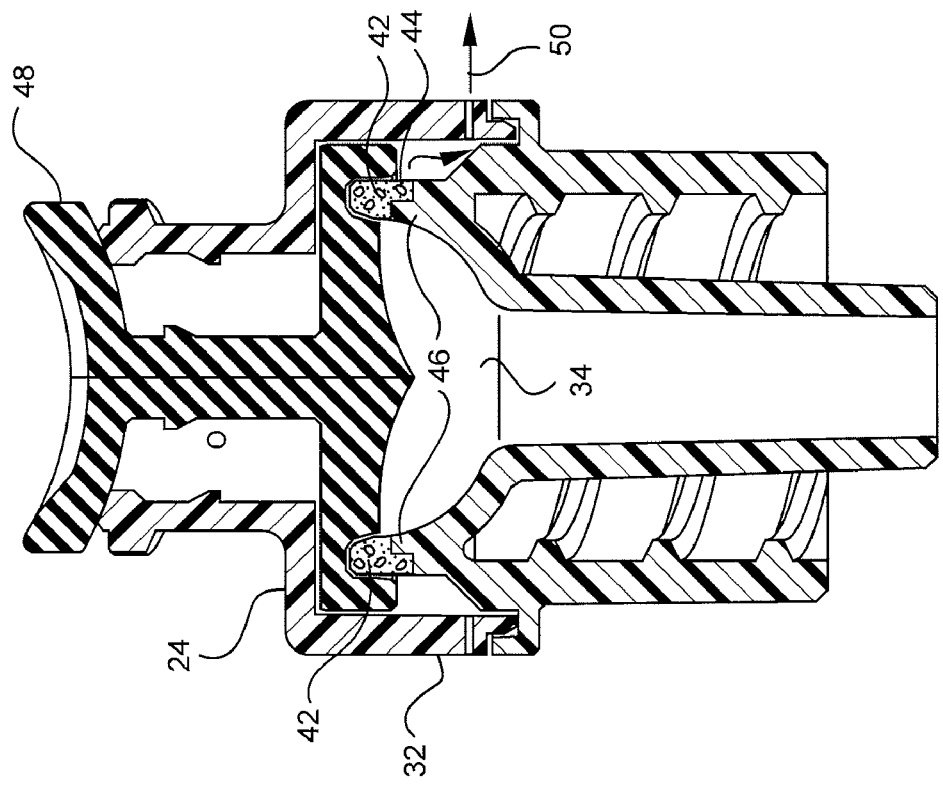
FIG. 5 is a cross section view of a Luer access device having an annular ring fit within a space of the housing of the device.

Referring now to FIG. 5, a Luer access device 24 includes a vent having an annular ring 52 fit within a space between the various portions of the housing 32 of the device 24. In the present embodiment, the device 24 includes the annular ring 52 beneath the outer edge 54 of the bottom disc 56 of a septum 48 of the device 24 and between two separate portions of the housing 32. The ring 52 may be manufactured of a porous plastic material such as Porex, GOR-TEX®, hydrogel, hydrophobic material, or any other venting material discussed throughout this disclosure. Any of the vents discussed within this disclosure may include any venting material discussed within this disclosure.

The ring 52 may be added to the device 24 during its manufacture prior to welding the various portions of the housing 32 together. In addition, various notches 58 may be added within the housing 32 of the device 24 in order to provide greater communication of gas from an internal cavity 34 of the device 24 to the annular ring 52 of the vent and ultimately to the external atmosphere of the device 24. The vent including the annular ring 52 may preferably include a material which is permeable to gas but capable of acting as a barrier to liquid, thus preventing blood from escaping the device 24 during its use in association with an extravascular system 10.

Figure 6A:
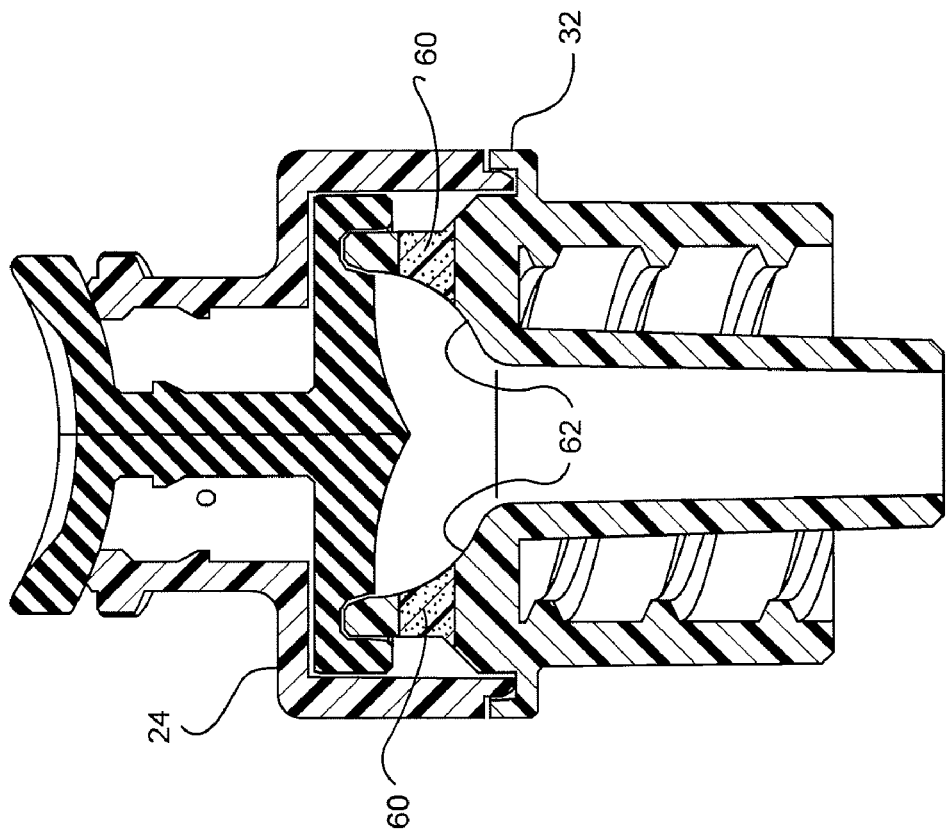
FIG. 6A is a cross section view of the Luer access device of FIG. 6 following curing of the vent material.
Figure 6:
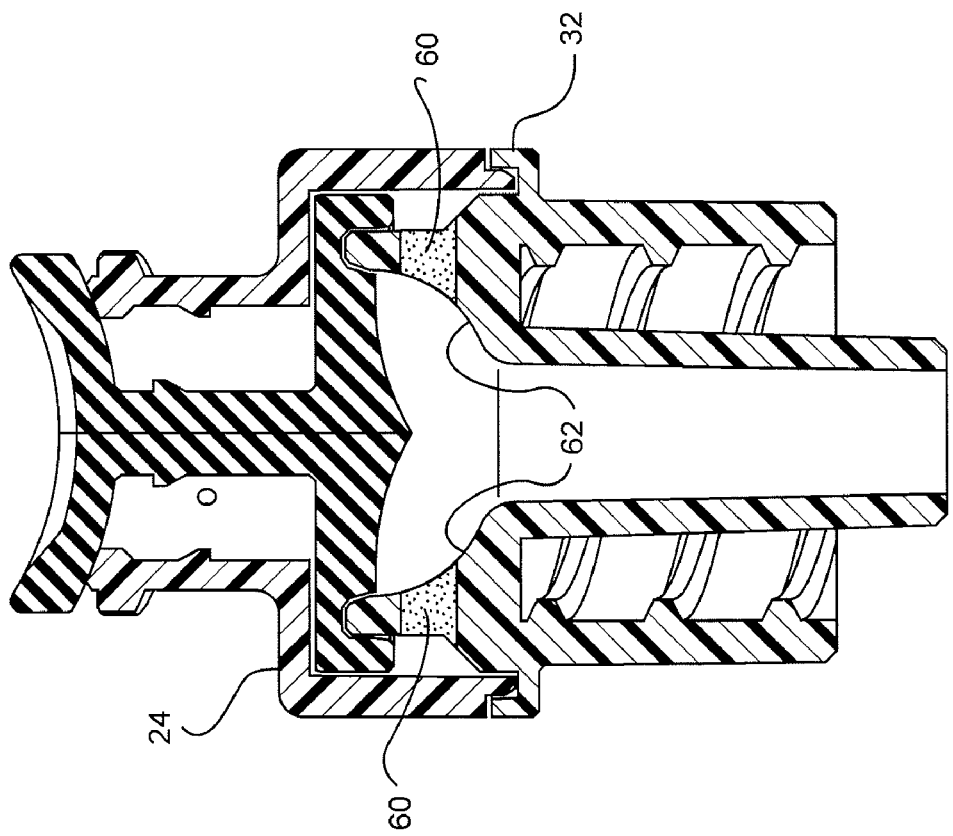
FIG. 6 is a cross section view of a Luer access device having an annular vent material.

Referring now to FIG. 6, a Luer access device 24 includes a vent with an annular vent material 60 that is exposed to an inner surface 62 of the Luer access device 24. The annular vent material 60 is a fluid curable material that begins to cure when blood comes into contact with the material 60. Such material 60 may be a Porex material coated with a curable powder, such as Portman cement or a powdered moisture cure adhesive.

The embodiment described with reference to FIG. 6 illustrates the vent material 60 before its contact with blood and resulting curing thereby, and after its contact with blood and resulting cure. By curing after coming into contact with blood, the vent material 60 provides a vent that is permeable to gas and capable of venting the device 24 of any gas this is contained therein in addition to any gas that is contained within an extravascular system 10 to which the device 24 may be attached. After the vent material 60 has vented all gas, the vent material will then come into contact with a liquid such as blood, causing the vent material to cure, and as a result, be no longer permeable to the passage of gas or liquid. FIG. 6A illustrates the vent material 60 after curing.

Figure 7:
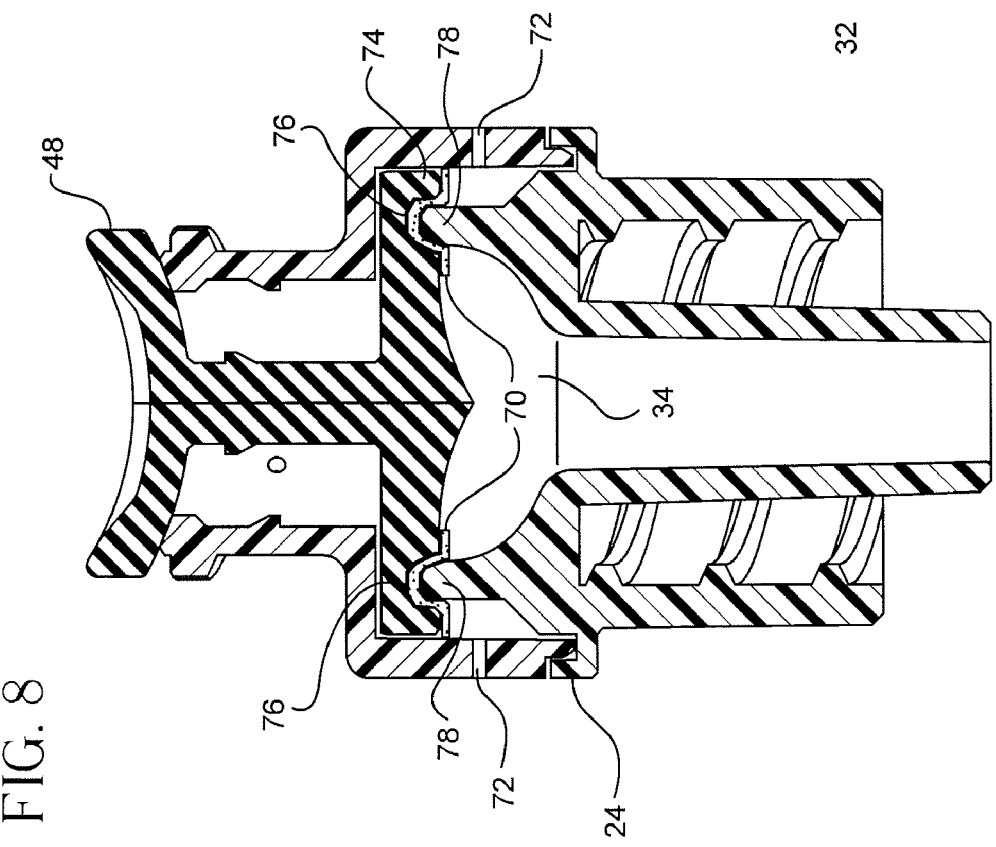
FIG. 7 is a cross section view of a Luer access device having a vent plug and a vent hole.

Referring now to FIG. 7, a Luer access device 24 includes a vent having a vent plug 64 and a vent hole 66. A venting material 68 is placed within the housing 32 of the device 24, adjacent to an internal cavity 34 in an air flow path from the internal cavity 34 to the external atmosphere. The venting material 68 of the vent plug 64 operates as a gas permeable vent capable of venting gas, but not liquid, from the internal cavity 34, through the vent plug 64, through the vent hole 66, and into the external atmosphere in which the device 24 is placed.

Figure 8:
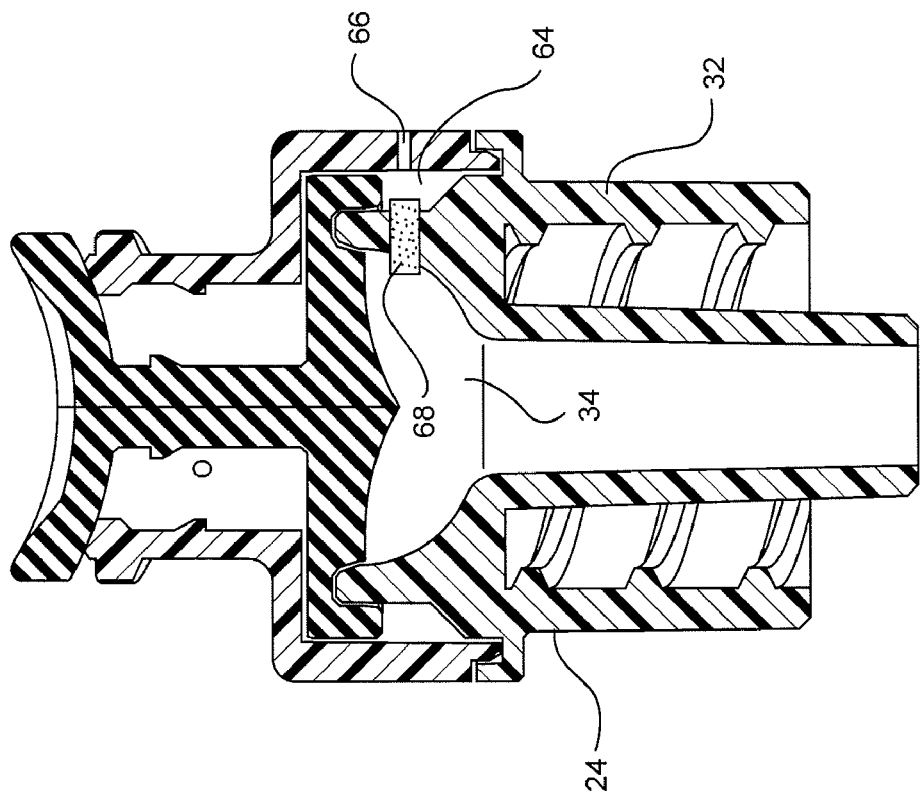
FIG. 8 is a cross section view of a Luer access device having an annular venting membrane secured at least in part by a septum.

Referring now to FIG. 8, a Luer access device 24 includes a vent with an annular venting membrane 70 secured at least in part by a septum 48 of the device 24. Similar to other vents described herein, the venting membrane 70 communicates with the housing 32 of the device 24 at a location in an air or gas flow path between an internal cavity 34 of the device 24 and the external atmosphere of the device 24. One or more vent holes 72 may be added to the air flow path of the device 24. As shown in FIG. 8, and similar to the annular ring 42 of FIG. 4, the venting membrane 70 is secured at least in part by a portion of the septum 48. In this example, an outer portion 74 of the bottom disc 56 of the septum 48 includes a recess 76 to which an extrusion 78 of the venting membrane is mechanically secured.

Figure 9:
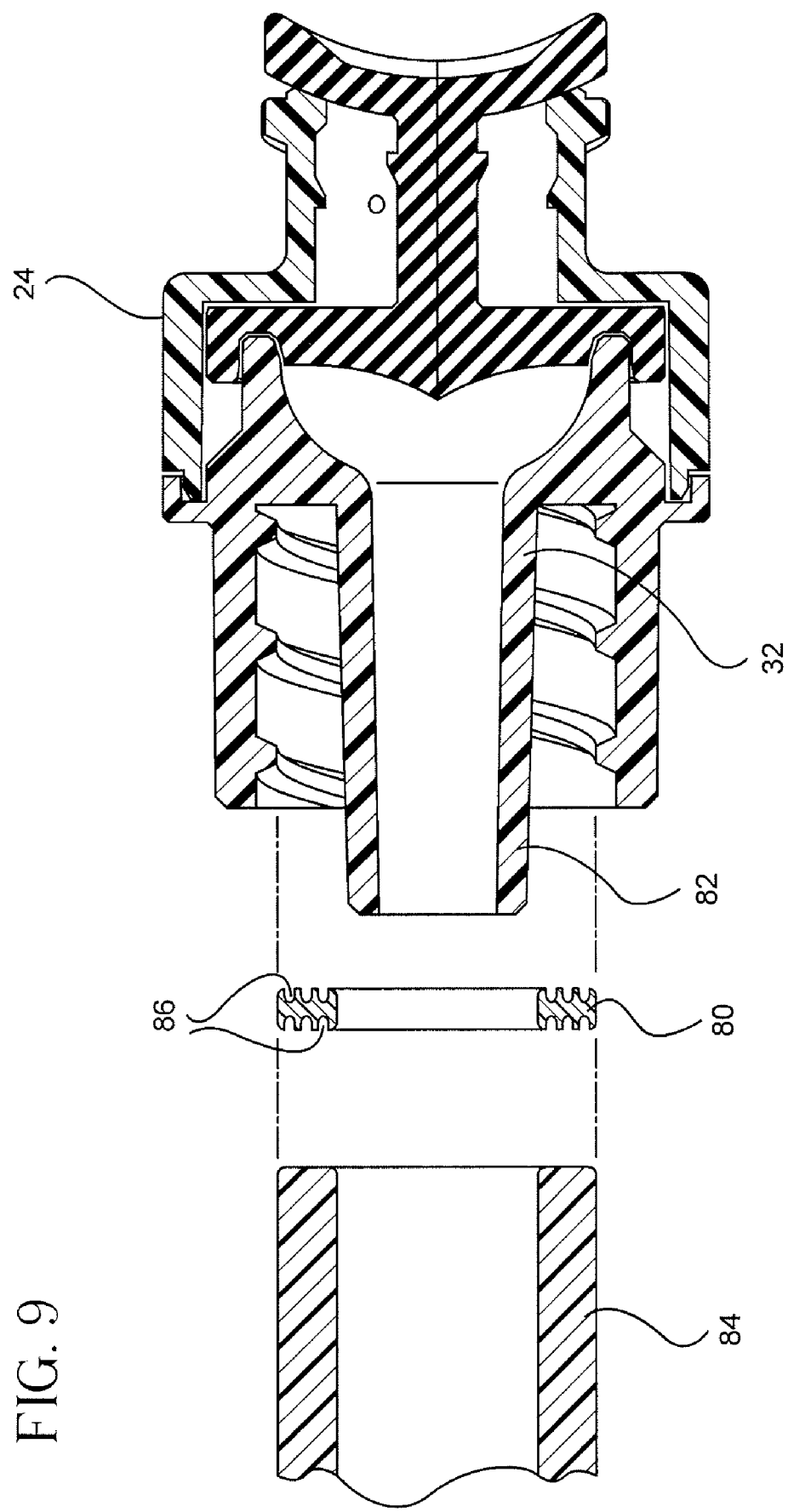
FIG. 9 is a cross section view of a Luer access device, a vent, and another vascular access device.

Referring now to FIG. 9, a Luer access device 24 may communicate with a gas permeable vent 80 between the threaded portion of the housing 32 that is adjacent to a male Luer 82 of the device 24 and a female connection of a catheter 84 or other vascular access device. The vent 80 is a disc of filter media or a silicon or polyisoprene washer with holes or grooves 86 in the surface of the vent 80.

The donut shaped vent 80 is placed over the male Luer end 82 of the device 24 so as to fit between the device 24 and the female Luer adapter 84 of a catheter, needle hub, extension set, or other vascular access device. The male Luer end 82 of the device 24, with the donut vent 80, is inserted into the female end 84 of the neighboring vascular access device so as to allow the vent 80 to contact the Luer end surfaces of both devices 24 and 84, but not to extend to seal the Luer tapers together. The vent 80 acts as a filter media for allowing venting of air or other gas to occur between the two Luer devices 24 and 84, but yet provides some seating force to prevent the Luer devices 24 and 84 from coming apart. The embodiment described with reference to FIG. 9 works particularly well for Luer lock devices including threads. After the venting has occurred between the two devices 24 and 84, the two Luer devices 24 and 84 can be tightened together so that the mating Luer surfaces of the devices 24 and 84 seal with each other.

The embodiment described with reference to FIG. 9 provides a means of venting existing Luer access devices without the need to redesign the devices. Constructing a vent 80 should require minimal cost and manufacturing difficulty. The vent 80 also provides a means for venting an extravascular system 10 of any gas contained therein while acting as a barrier to blood or other fluid which risks exiting the extravascular system 10, causing blood loss to a patient and potential contamination to an operator. Any venting material discussed in this disclosure and any venting material used in conventional medical IV bags, catheters, introducers, and other devices, may be used to provide the material for the vent 80.

Figure 10A:
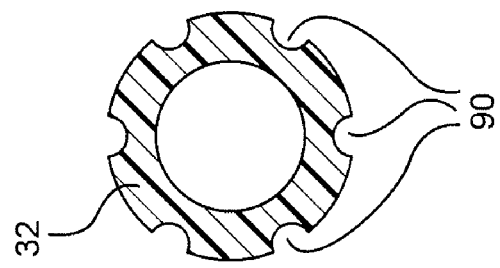
FIG. 10A is a cross section view of the tip of the Luer access device of FIG. 10 taken along lines 10A-10A.
Figure 10:
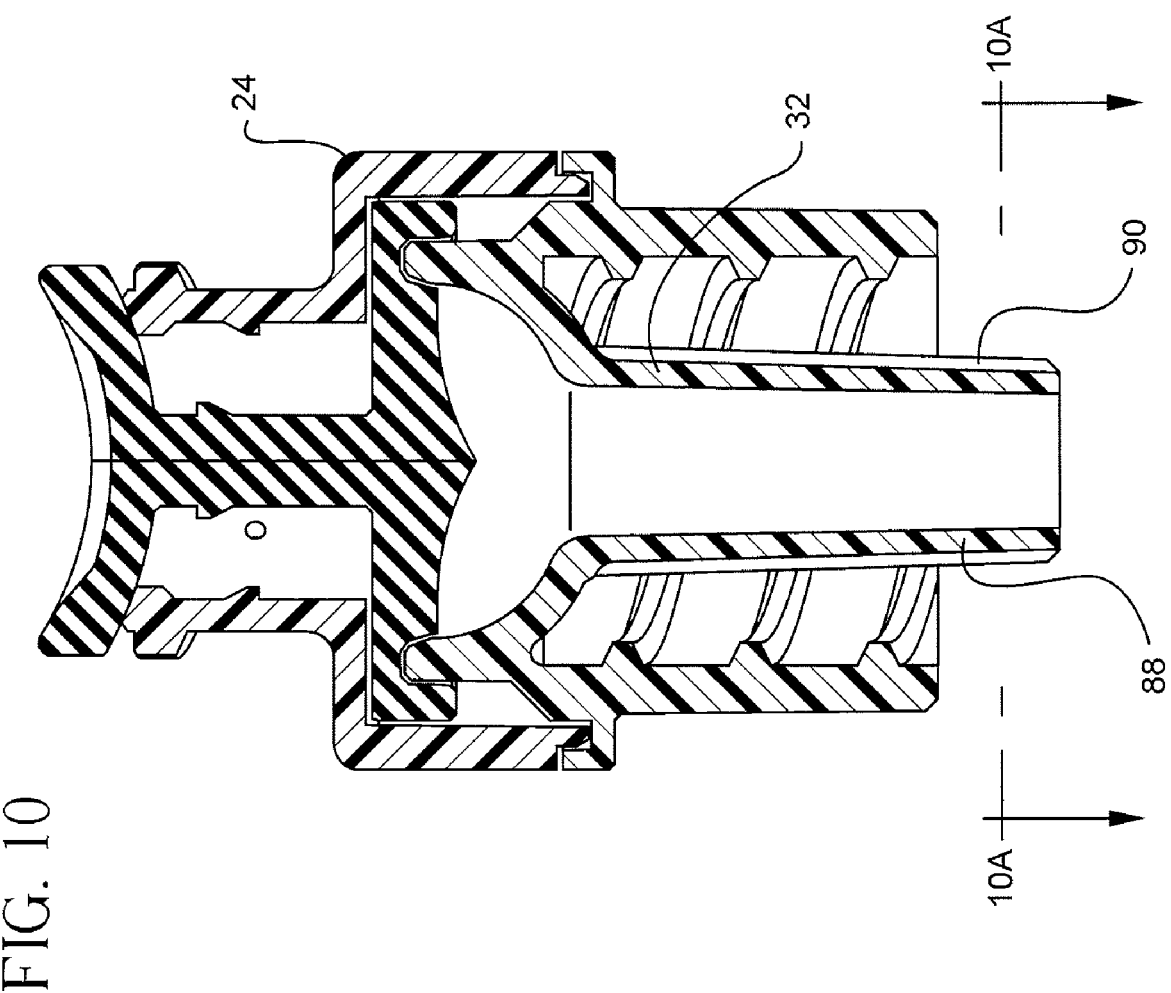
FIG. 10 is a cross section view of the tip of a Luer access device.

Referring now to FIG. 10, a Luer access device 24 includes a tip 88. The tip 88 of the device 24 may be used for insertion into any other vascular access device of an extravascular system 10, and includes at least one vent or vent insert 90 in the housing 32 of the tip 88. The vented inserts 90 may be formed of any vent material, including a porous material that allows air or other gas to pass but not fluid. The vented inserts 90 are placed on the external surface of the tip 88, providing a vent between the housing 32 of the tip and the housing of any other vascular access device that is connected to the device 24. In this manner, the vented inserts 90 will operate as a vent to air, but not liquid, for an extravascular system 10 including a vascular access device connected to the device 24. As shown in FIG. 10A, section 10A-10A taken along lines 10A-10A of FIG. 10 illustrates a top cross section view of the tip 88, showing the vented inserts 90 within the external surface of the housing 32.

Figure 11:
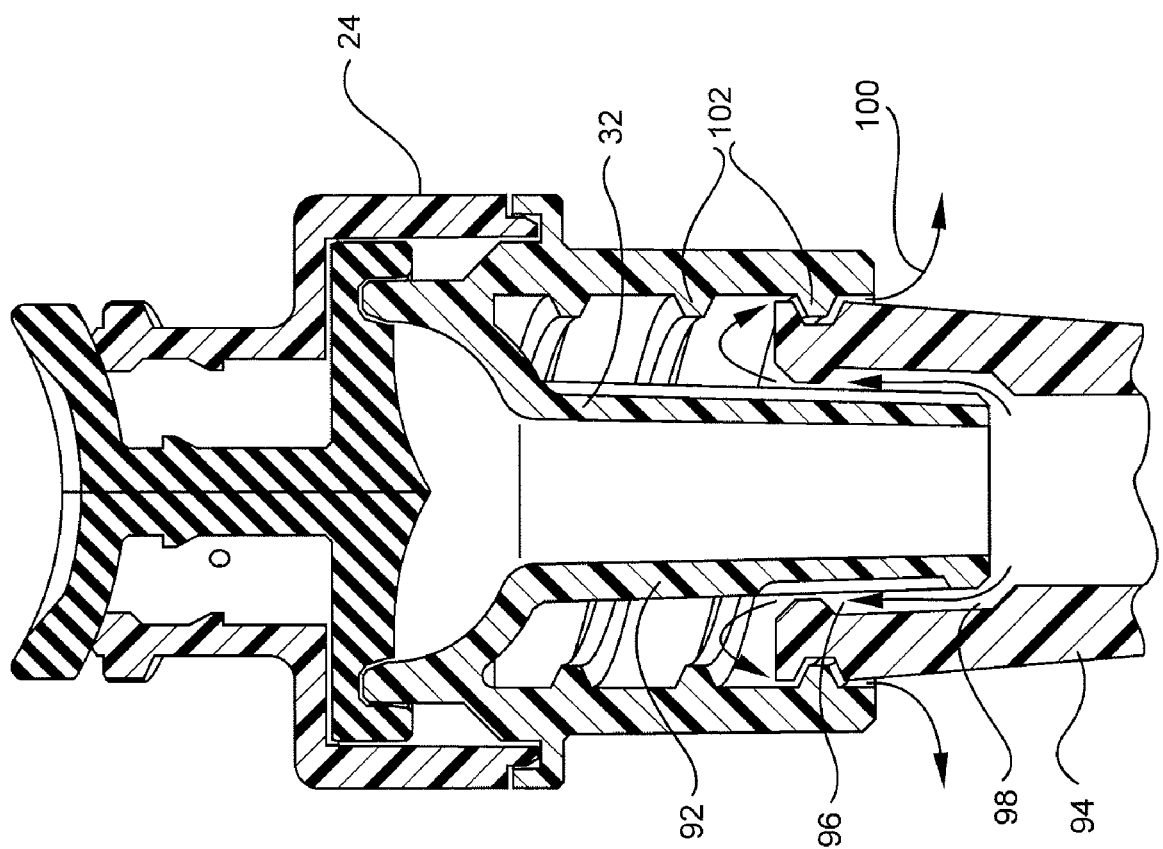
FIG. 11 is a cross section view of a Luer access device sharing a vent with another vascular access device.
Figure 11:

Referring now to FIG. 11, a Luer access device 24 includes a tip 92 for access into the female end of another vascular access device 94. A vent is located in at least a part of the housing 32 of the tip 92. The vent is a channel 96 formed within the exterior surface of the tip 92. A corresponding channel 98 is formed within the interior surface of the female end of another vascular access device 94. When the device 24 is initially connected to the device 94, the channels 96 and 98 overlap creating an air flow path 100 at the connection between the devices 24 and 94 through which gas may escape the extravascular system 10 of which the devices 24 and 94 are a part. The channels 96 and 98 should extend just over half the distance of the Luer surfaces of the devices 24 and 94 so that if the two mating Luers are aligned with the channels 96 and 98 facing each other, a continuous air flow path 100 is created to allow the trapped air within the system 10 to vent.

When the mating Luers of the devices 24 and 94 are tightened or twisted so that the channels 96 and 98 are no longer facing each other, the connection between the devices 24 and 94 become sealed, interrupting the air flow path 100. The channels 96 and 98 on each mating device 24 and 94 should be oriented so that the Luer surfaces of the devices 24 and 94 have some minimal contact to keep the two devices 24 and 94 together, but still allow for further tightening along the threads 102 of the devices 24 and 94. The embodiment described with reference to FIG. 11 works particularly well with Luer lock devices having threads. The channels 96 and 98 in each Luer surface should be small enough to allow air to pass freely, but impede fluid or other blood flow. The channels 96 and/or 98 may also include any venting material discussed in this disclosure.

Figure 12:
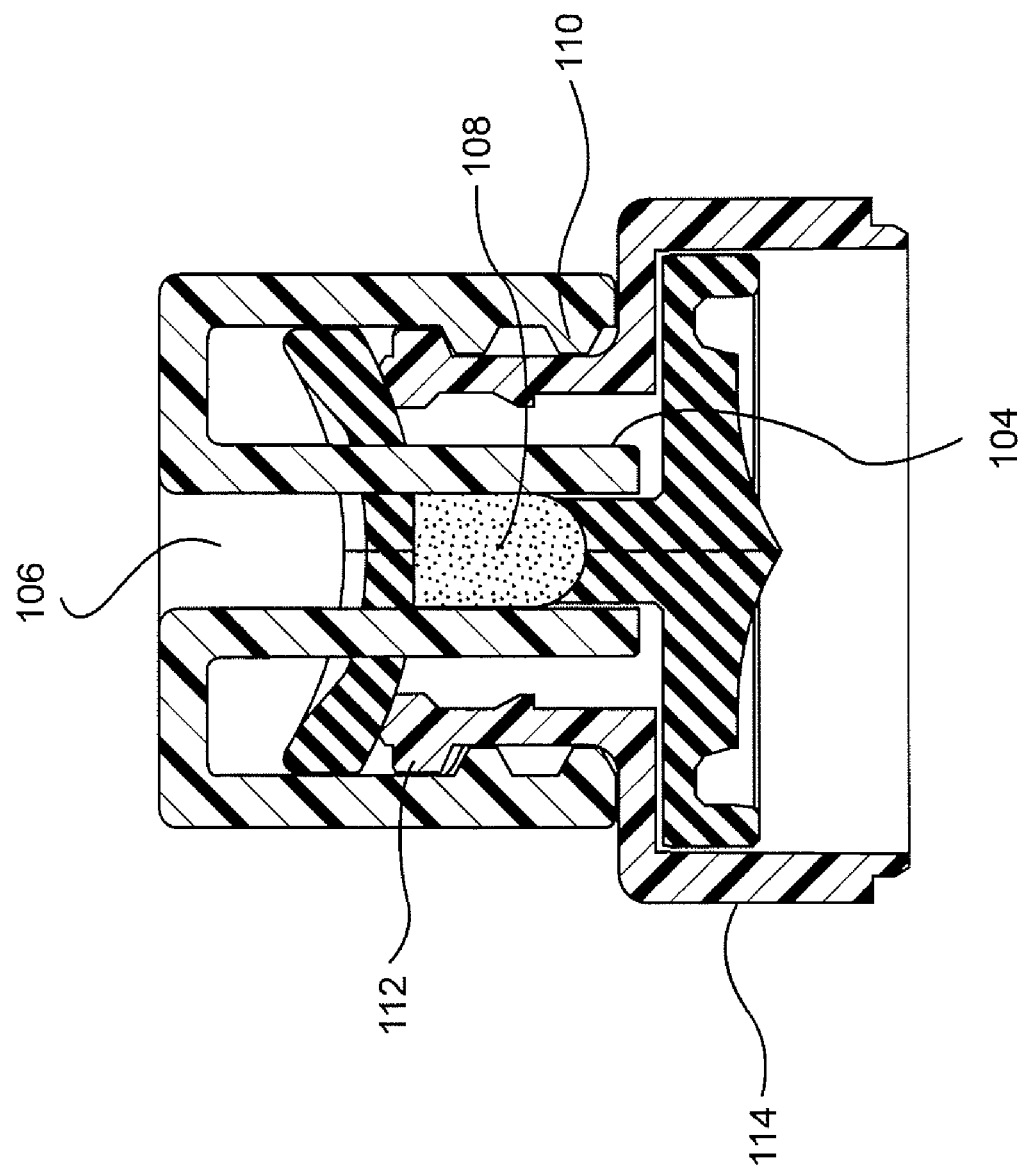
FIG. 12 is a cross section view of a Luer access device secured to another vascular access device.
Figure 14:
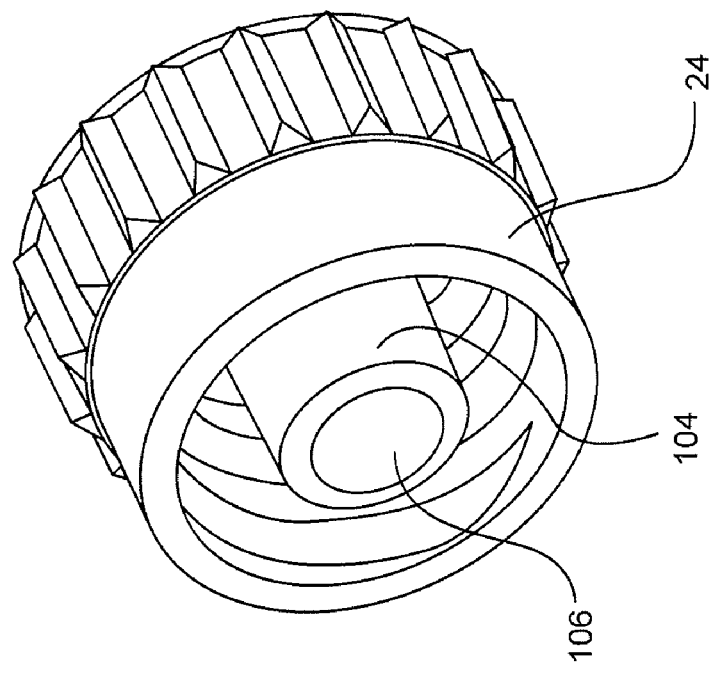
FIG. 14 is an alternate perspective view of the Luer access device of FIG. 12.
Figure 13:
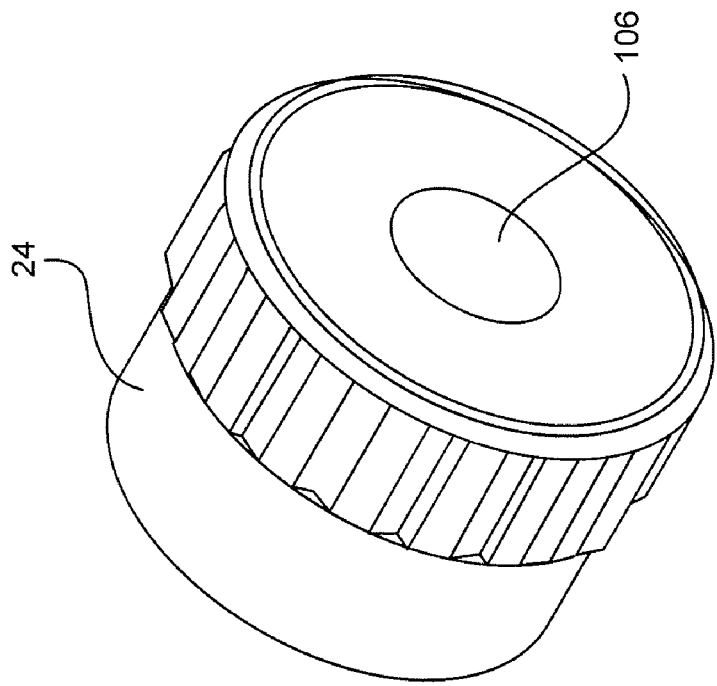
FIG. 13 is a perspective view of the Luer access device of FIG. 12.

Referring now to FIG. 12, a Luer access device 24 includes a tip 104 having a lumen 106 and a vent 108 residing within the lumen 106. The vent may be any filter or venting material discussed within this disclosure. The device 24 may also include threads 110 capable of connecting with corresponding threads 112 of another vascular access device 114. Thus, the tip 104 of the device 24 may penetrate into the female end of another vascular access device 114, exposing the vent 108 to gas trapped within or traveling through the interior of the other vascular access device 114. FIGS. 13 and 14 show alternate perspective views of the device 24 described with reference to FIG. 12. The embodiment described with reference to FIGS. 12 through 14 thus provides a Luer access device that includes a tip 104 having a lumen 106 with a vent 108 residing within the lumen 106. The Luer access device 24 may simply operate as a venting device without providing access to any Luer or other vascular access device.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device, comprising:
    A vascular access device, including a housing defining an internal cavity, and a septum;
    an air flow channel penetrating the housing and providing continuous gaseous communication between the internal cavity and an external environment;
    a vent in communication with the internal cavity;
    a vent plug, which is impermeable to gas, attached to a gas permeable membrane, wherein the gas permeable membrane and vent plug are selectively movable from a first open position to a second closed position, wherein the gas permeable membrane is at least partially disposed within the vent in the first open position;
    wherein the vent is capable of venting a gas from an extravascular system into the air flow channel.

2. The medical device of claim 1, wherein the vent includes a vent plug and a vent hole.

3. The medical device of claim 1, wherein the vent communicates with a vascular access device secured to the access device.

4. A method of venting a medical device, comprising:
    providing a vascular access device, wherein the vascular access device includes a housing defining an internal cavity, and a septum, and forms part of an extravascular system;
    providing a gas permeable vent in communication with at least a portion of the housing and an air flow channel maintained spaced from the vent and penetrating the housing such that air can selectively flow into and out of the device, wherein the vent includes a gas permeable membrane attached to a vent plug which is impermeable to gas, wherein the membrane and vent plug are selectively movable from a first open position to a second closed position; and venting gas from the extravascular system through the gas permeable vent of the access device and through the air flow channel to an external environment.

5. The method of claim 4, wherein the vent includes a vent plug and a vent hole.

6. The method of claim 4, further comprising cutting off gas venting by moving the vent plug to the second closed position in which the vent plug is at least partially within the vent.

7. The method of claim 4, wherein the movable vent plug and the membrane move from a first open position to a second closed position in response to a force directed from an external environment toward the housing.

8. A vascular access device comprising:
a housing having an interior lumen extending through the housing;
a gas communication channel extending between the exterior of the housing and the lumen;
a gas permeable membrane; and
a movable vent plug attached to the gas permeable membrane, wherein the gas permeable membrane and the moveable vent plug are selectively moved from a first open position to a second closed position, wherein the gas permeable membrane is partially disposed within the gas communication channel when in the first open position and the vent plug is partially disposed within the gas communication channel when in the second closed position.

* * * * *